US012708250B2

(12) United States Patent
Tang et al.

(10) Patent No.: US 12,708,250 B2
(45) Date of Patent: Aug. 18, 2026

(54) MEDICAL CONNECTING DEVICE

(71) Applicant: Micro-Tech (Nanjing) Co., Ltd., Nanjing (CN)

(72) Inventors: Zhi Tang, Nanjing (CN); Mingqiao Fan, Nanjing (CN); Huan Xie, Nanjing (CN); Deqing Sha, Nanjing (CN); Changqing Li, Nanjing (CN); Derong Leng, Nanjing (CN); Chunjun Liu, Nanjing (CN)

(73) Assignee: Micro-Tech (Nanjing) Co., Ltd., Nanjing (CN)

( * ) Notice: Subject to any disclaimer, the term of this patent is extended or adjusted under 35 U.S.C. 154(b) by 963 days.

(21) Appl. No.: 17/289,017

(22) PCT Filed: Feb. 25, 2019

(86) PCT No.: PCT/CN2019/076046
§ 371 (c)(1),
(2) Date: Apr. 27, 2021

(87) PCT Pub. No.: WO2020/103350
PCT Pub. Date: May 28, 2020

(65) Prior Publication Data

US 2022/0000344 A1 Jan. 6, 2022

(30) Foreign Application Priority Data

Nov. 21, 2018 (CN) ........................ 201811390053.3

(51) Int. Cl.
*A61B 1/00* (2006.01)
*A61M 25/00* (2006.01)
(Continued)

(52) U.S. Cl.
CPC ..... *A61B 1/00128* (2013.01); *A61M 25/0045* (2013.01); *A61B 1/00119* (2013.01);
(Continued)

(58) Field of Classification Search
CPC ...... A61B 1/00128; A61B 2017/00309; A61B 10/0283; A61B 34/70; A61B 18/1445;
(Continued)

(56) References Cited

U.S. PATENT DOCUMENTS 4,586,923 A * 5/1986 Gould ............... A61M 25/0147 604/95.04
5,030,204 A * 7/1991 Badger ............ A61M 25/0152 604/95.04
(Continued)

FOREIGN PATENT DOCUMENTS

CA 2284784 A1 * 7/1999 ............. A61M 1/00
CN 103750901 A 4/2014
(Continued)

OTHER PUBLICATIONS

Machine translation of CN 108514677 from WIPO (Year: 2018).*
(Continued)

*Primary Examiner* — Emily L Schmidt
*Assistant Examiner* — Samuel J Marrison
(74) *Attorney, Agent, or Firm* — Mandar A. Joshi; Bret E. Field; Bozicevic, Field & Francis LLP

(57) ABSTRACT

A medical connecting device, having a proximal end and a distal end; the medical connecting device includes an insulating layer (3, 123, 222, 322) and a spiral tube (2, 124, 223, 323), the insulating layer (3, 123, 222, 322) covering the outermost layer of the whole device; the spiral tube (2, 124, 223, 323) has a conductive hollow tubular structure; and the spiral tube (2, 124, 223, 323) has a spiral structure, and a pitch of the spiral structure gradually changes in the direction from the proximal end to the distal end. The medical connecting device is able to integrate multiple functions
(Continued)

such as electricity conducting, liquid passage, powder spraying, negative pressure suction, sealing, insulation, and support.

16 Claims, 3 Drawing Sheets

(51) Int. Cl.
*A61B 10/02* (2006.01)
*A61B 18/14* (2006.01)

(52) U.S. Cl.
CPC ....... *A61B 10/0283* (2013.01); *A61B 18/1442* (2013.01); *A61M 25/005* (2013.01)

(58) Field of Classification Search
CPC ........ A61B 2018/00077; A61B 18/148; A61B 18/1482; A61B 18/1485; A61B 18/1487; A61B 18/1492; A61B 18/1477; A61B 18/149; A61M 25/005; A61M 25/0051; A61M 25/0053; A61M 25/0054; A61M 2025/0018; A61M 2025/09066; A61M 2025/09075; A61M 2025/09083; A61M 2025/091; A61M 2025/09125; A61M 2025/0915; A61M 2025/09191; A61M 25/0023; A61M 25/0028
See application file for complete search history.

(56) References Cited

U.S. PATENT DOCUMENTS 5,137,013 A * 8/1992 Chiba ...................... F16F 1/04 604/524
5,571,085 A * 11/1996 Accisano, III .... A61M 25/0136 604/95.01
5,913,854 A * 6/1999 Maguire ............ A61B 18/1492 606/41
6,217,549 B1 * 4/2001 Selmon ................ A61M 29/02 604/105
2003/0069522 A1 * 4/2003 Jacobsen ........... A61M 25/0051 600/585
2004/0122360 A1 * 6/2004 Waldhauser ........ A61M 25/005 264/234
2013/0310833 A1 11/2013 Brown et al.
2015/0265262 A1 9/2015 Dewaele et al.
2016/0249788 A1 * 9/2016 Saito ................ A61M 25/0053 600/140
2018/0028263 A1 2/2018 Keady et al.

FOREIGN PATENT DOCUMENTS

CN 203988348 U 12/2014
CN 204158527 U 2/2015
CN 105395251 A 3/2016
CN 108272503 A 7/2018
CN 108514677 A 9/2018
CN 108742832 A 11/2018
CN 209611076 U 11/2019

OTHER PUBLICATIONS

First Korean Office Action for corresponding Korean Patent Application No. 20-2021-7000029, mailed on Feb. 17, 2023, and its English translation, 11 pages.
First Spanish Office Action for corresponding Spanish Patent Application No. P202190026, mailed on Oct. 25, 2022, and its English translation, 16 pages.
First Office Action for corresponding Chinese Patent Application No. 201811390053.3, mailed Nov. 18, 2024, and its English translation, 15 pages.

* cited by examiner

MEDICAL CONNECTING DEVICE

FIELD OF THE PRESENT DISCLOSURE

The present disclosure relates to a medical connecting device in the field of medical instruments, and more particularly, to a device as an accessory for an endoscope, which integrates multiple functions such as electricity conducting, liquid passage, powder spraying, negative pressure suction, sealing, insulation, and support.

BACKGROUND OF THE PRESENT DISCLOSURE

Endoscopic technique has progressed from disease diagnosis to disease treatment in the past 50 years and has been established as a quite effective and reliable treatment to some digestive diseases, even as the first choice of treatment. With the development of endoscopic technique in recent years, endoscopic tissue biopsy, endoscopic mucosal resection (EMR), and endoscopic submucosal dissection (ESD) have been widely used, and are gradually becoming the first choice of the treatment to gastrointestinal bleeding, polypectomy, and early cancers. In particular, ESD plays a key role in the discovery, diagnosis, and resection of early cancers.

In various clinical departments, direct observation and treatment in vivo are required for the diagnosis, prognosis, treatment protocols of various diseases. Previously, all these required invasive surgical procedures such as laparotomy or thoracotomy. However, with the popularity of endoscopic surgical instruments in recent years, they can be performed with a laparoscope or a thoracoscope in a minimally invasive manner.

Endoscopic submucosal dissection (ESD) is an endoscopic minimally invasive procedure for submucosal dissection of lesions larger than 2 cm using high-frequency instruments. A large area of the mucosa is resected through ESD, and the procedure is complicated, generally time-consuming, and requiring endoscopic guidance. The endoscope firstly enters the human body to find a pathological tissue, and a high frequency electric knife enters the human body via an endoscope channel and mark pathological changes. After this, the instrument is withdrawn, and an injection needle is used to for submucosal injection. After injection, a proper high frequency electric knife resects the pathological tissue. If bleeding happens in the procedure, the hemostat forceps needs to be used for electrocoagulation hemostasis. As such, it takes 1 to 2 hours to successfully resect an early cancer of about 3 cm. Frequent replacement of the instruments takes place in the procedure, which slows down the procedure and intensifies the pain of the patient. A product integrating the functions of marking, flushing, injection, resection, hemostasis, and the like is desirable for such complicated procedures under the endoscope. Therefore, the connecting device for such a product should have high functionality, otherwise, frequent replacement of instruments leads to a longer procedure.

The conventional connecting tube as an accessory for an endoscope is single in functionality, can only realize a part function, and lacks versatility. For example, the connecting tube for the injection needle is generally made of polymer materials, which can realize the liquid passage function, but cannot realize the electricity conducting function. For another example, the connecting tube for the high frequency electric knife is sometimes a stainless steel tube, which realizes the function of liquid passage and electricity conducting, but has a uniform overall structure with a hard front end, resulting in difficulty in passing through a curved channel of the endoscope. For yet another example, the connecting tube for the hemostat forceps is generally made of a solid stainless steel wire or a stainless steel cable, which can only realize the electricity conducting function, but cannot realize the liquid passage function. For still another example, the coated spring tube in the prior art is generally formed by winding spring wires, whereby the overall structure features are the same from the front end to the rear end, unable to achieve both flexibility and rigidity. In pursuit of better functionality of the endoscope accessory product, it is desirable to develop a medical connecting device capable of integrating multiple functions such as electricity conducting, liquid passage, powder spraying, negative pressure suction, insulation, sealing, and support, achieving both flexibility and rigidity.

SUMMARY OF THE PRESENT DISCLOSURE

An end near an operator is defined as a proximal end, and an end remote from the operator is defined as a distal end.

A medical connecting device, having a proximal end and a distal end, and including an insulating layer and a spiral tube, the insulating layer covering an outermost layer of the device; wherein the spiral tube has a conductive hollow tubular structure positioned at the inner layer of the device, the spiral tube has a spiral structure having a pitch that gradually changes from the proximal end to the distal end. The pitch may gradually decrease from the proximal end to the distal end. A smaller pitch at the distal end makes it flexible and easy to pass through a curved channel of a medical apparatus, and a larger pitch at the proximal end provides support and facilitates pushing medical instruments to the distal end. The pitch may gradually increase from the proximal end to the distal end, wherein the distal end has a larger pitch, and the proximal end has a smaller pitch. The pitch may also increase and then decrease from the proximal end to the distal end, or decrease and then increase from the proximal end to the distal end, or an equal-pitch configuration is adopted. A gap between the spiral structures is not less than 0.003 mm, and the pitch of each thread is not less than 0.03 mm. Preferably, the spiral tube is a material having electrical conductivity.

The spiral tube has the spiral structure from the proximal end to the distal end entirely. It is also contemplated that the proximal and distal ends of the spiral tube may each or both have a partially non-spiral structural region. The spiral tube can adopt an equal-pitch configuration, a gradual-pitch configuration, a combination of various equal-pitch configurations, and a combination of the equal-pitch and the gradual-pitch configurations.

The medical connecting device of the present disclosure also includes one or more seals connected with either or both of the distal end and the proximal end of the spiral tube. The seal is of a non-planar structure and can be of a concave-convex type, a concave type, or a convex type. A convex portion of the non-planar structure may be a semicircle, a rectangle, a trapezoid, or a toothed shape.

The insulating layer of the present disclosure is made of a polymer material and has a thickness not less than 0.03 mm. The polymer material is polytetrafluoroethylene, fluoroethylene propylene copolymer, or polyethylene. The insulating layer is coated on an outer surface of the spiral tube through pyrocondensation, welding, pasting, or the like.

The medical connecting device of the present disclosure includes the insulating layer, the spiral tube, and the seal.

The insulating layer is positioned on the outer layer of the device, providing insulation and protection function, and also has a sealing effect. The spiral tube has an electricity conducting function, and also provides a lumen channel, realizing the liquid injection function and the like. The spiral tube includes the spiral structure, the orientation of the spiral structure is not fixed, different pitches can be designed according to different requirements, and the spiral tube can be used for liquid injection, powder spraying, sampling through negative pressure suction, and the like. The end having the smaller pitch of the medical connecting device is flexible and easy to pass through a channel of an endoscope, and the end having the larger pitch is relatively rigid and provides support performance. The distal and proximal ends have partially non-spiral structural regions. A shorter non-spiral structural region can reduce the length of a rigid section of the product. A longer non-spiral structural region facilitates pushing the device. The seal is of a non-planar structure, including various types such as a concave-convex type, a concave type, or a convex type. The seal can be connected with the spiral tube to realize the sealing function. When the non-spiral structural region at one end of the spiral tube is relatively long, the seal can be only connected at the other end of the spiral tube. When the lengths of the non-spiral structural regions at both ends are the same or similar, the seal can be connected at both ends of the spiral tube. The insulating layer covers the seal on the outer side of the seal, the pressure is gradually reduced through the non-planar structure of the seal, and the sealing effect is improved.

The insulating layer is arranged on the outermost layer of the whole device. The spiral tube is of a hollow tubular structure made of a material with electrical conductivity and is positioned at an inner layer of the whole device, and the spiral tube includes the spiral structure.

The insulating layer is made of a polymer material, and covers the surfaces of the spiral tube and the seal. The material includes but is not limited to polytetrafluoroethylene (PTFE), fluoroethylene propylene copolymer (FEP), and polyethylene (PE), and has a thickness of not less than 0.03 mm. The insulating layer is attached to the surface of the spiral tube through pyrocondensation, welding, pasting, or the like. The insulating layer provides the product with good pressure resistance, with a dielectric performance not lower than 300 Vp, and the product has a desirable sealing performance, capable of bearing a pressure not lower than 2 atm.

The spiral tube is made of conductive materials to enable the electricity conducting function, and the lumen channel is provided to enable the liquid injection and powder spraying functions. One end of the hollow structure is connected with an electric part of an instrument, such as an electrode, a hemostat head, and a needle-shaped structure, to enable the functions of resection, hemostasis, and the like of the product. The spiral tube has an outer diameter of not less than 0.3 mm and a wall thickness of not less than 0.05 mm. Since the wall thickness of the spiral tube is small, a large lumen space can be provided. The spiral tube with a small outer diameter contributes to a reduced outer diameter of the whole instrument, which facilitates the operation and adapts the product to a smaller endoscope lumen. In addition, compared with a common wound spring tube, the spiral tube has a smaller resistance value of not greater than 20Ω, allowing higher electricity in the instrument under the same voltage, and improving the working efficiency. The outer layer of the spiral tube is covered with the insulating layer, so that a user is effectively protected from being injured by electric shock.

The spiral tube adopts a hollow tubular structure and thus provides a channel, enabling the functions of liquid passage, powder spraying, negative pressure suction, and the like. Injection of normal saline and indigo carmine, powder spraying, or sampling through negative pressure suction and the like can be realized clinically. The spiral tube is provided with the spiral structure, preferably, the pitch at the distal end of the spiral tube is small and provides elasticity, which provides good curving performance, and the product is facilitated to pass through the bent endoscope lumen channel. The pitch at the proximal end of the spiral tube is large, which provides good support performance. In addition, the pitch can be adjusted according to different requirements on flexibility, to adapt to requirements on different products. The pitch of each thread of the spiral tube can adopt an equal-pitch configuration, a gradual-pitch configuration (the pitches can be an equal-difference sequence), a combination of various equal-pitch configurations, a combination of the equal-pitch and the gradual-pitch configurations, and the like. Other different spiral structures can also be contemplated as per requirements. Preferably, a combination of the equal-pitch and the gradual-pitch configurations may be selected.

DESCRIPTION OF THE EMBODIMENTS

In order that the objects, aspects, and advantages of the present disclosure will become more apparent, the present disclosure will be described in further detail with reference to the accompanying drawings and embodiments. It is to be understood that the specific embodiments described herein are merely illustrative of the present disclosure and are not intended to be limiting thereof. The scope of the application is not limited by the embodiments, but rather by the claims. To provide a clearer description and to enable those skilled in the art to understand the application, it is not necessary that portions of the drawings be drawn in their relative dimensions, that some dimensions may be exaggerated in proportion to other relevant dimensions, and that irrelevant or unimportant details may not be fully shown for the brevity of illustration.

The device of the present disclosure may be used in but is not limited to the following embodiments, and may also be used in other endoscopic consumables, such as a combined instrument of scalpel and hemostat forceps, a bipolar probe, and a combined instrument of probe and entry needle.

Also, the medical connecting device can adopt different sizes, and multiple medical connecting devices with multiple sizes can be combined and matched in one product.

Figure 1A:
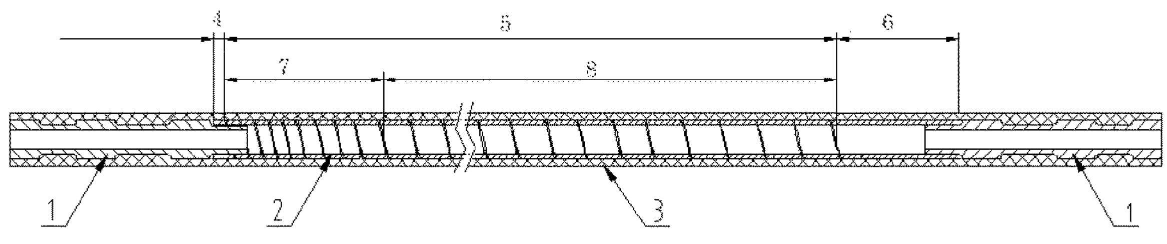
FIG. 1A is a schematic view of distal and proximal ends connected with a seal, respectively, of the spiral tube of the device of the present disclosure.
Figure 1B:
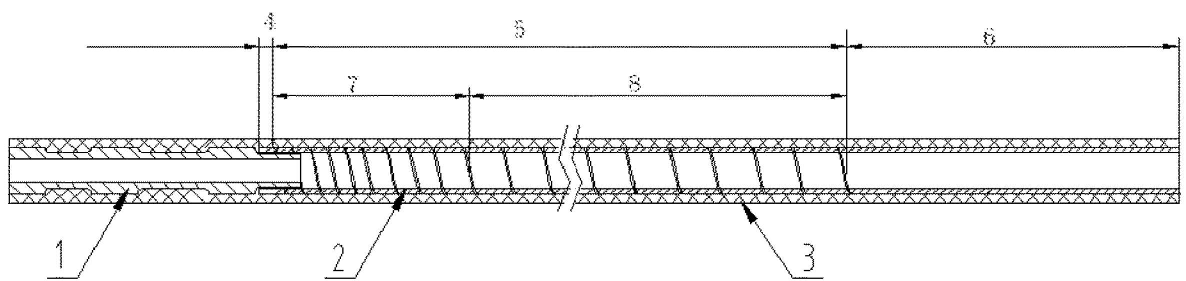
FIG. 1B is a schematic view of the distal end connected with the seal, of the spiral tube of the device of the present disclosure.
Figure 5:
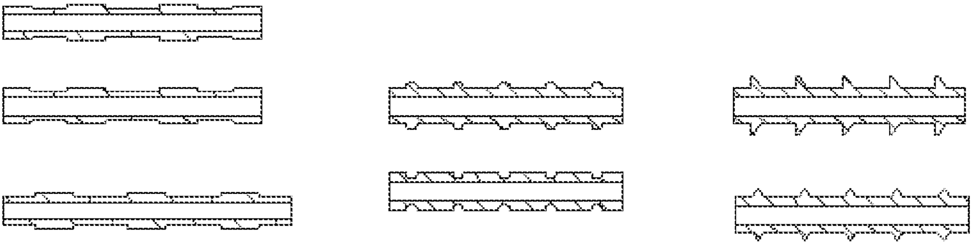
FIG. 5 is a structural view of the seal of the device of the present disclosure.

As shown in FIGS. 1A and 1B, the medical connecting device of the present disclosure includes: a spiral tube 2, a seal 1, and an insulating layer 3 covering on outer surfaces of the spiral tube 2 and the seal 1. The spiral tube 2 includes a spiral structure, and different pitches can be designed according to different requirements. Preferably, the spiral tube 2 includes a distal non-spiral structural region 4, a proximal non-spiral structural region 6, and a middle spiral structural region 5. A spiral structure 8 near the proximal end is designed to have an equal-pitch configuration, and a spiral structural region 7 near the distal end has a pitch that decreases from the proximal end to the distal end. It is also possible that the middle spiral structural region 5 is designed to have a pitch that gradually decreases from the proximal end to the distal end. It is also possible to adopt a configuration in which the pitch decreases and then increases from the proximal end to the distal end, a combination of various equal-pitch configurations, a combination of the equal-pitch and the gradual-pitch configurations, etc. It is also possible to design other different spiral structures (not shown) according to requirements. The distal non-spiral structural region is short, which shortens a rigid section of the product. The pitch at the distal end is small, which renders flexibility, and facilitates passing through a medical apparatus such as a curved channel of an endoscope. The pitch at the proximal end is large and provides good support performance. The proximal non-spiral structural region is long, which facilitates pushing. The middle portion and the proximal end are relatively rigid, which provides support performance. The spiral tube 2 can have the electricity conducting function, and provides a lumen channel, enabling the functions of liquid injection and the like. As shown in FIG. 1A, when the lengths of the distal non-spiral structural region 4 and the proximal non-spiral structural region 6 are similar, both ends of the spiral tube 2 may be provided with the seal 1. As shown in FIG. 1B, when the proximal non-spiral structural region 6 of the spiral tube 2 is longer, the spiral tube 2 is connected with the seal 1 only at the distal end. The insulating layer 3 covers on the outer surfaces of the spiral tube 2 and the seal 1, which provides insulation and protection function, and also has a sealing effect. FIG. 5 is a schematic view showing a structure of the seal, which is a non-planar structure of various types such as a concave-convex type, a concave type, and a convex type. A convex portion of the non-planar structure may be a semicircle, a rectangle, a trapezoid, or a toothed shape. The seal 1 can be connected with the spiral tube 2 to realize a sealing function.

Embodiment 1

Figure 2:
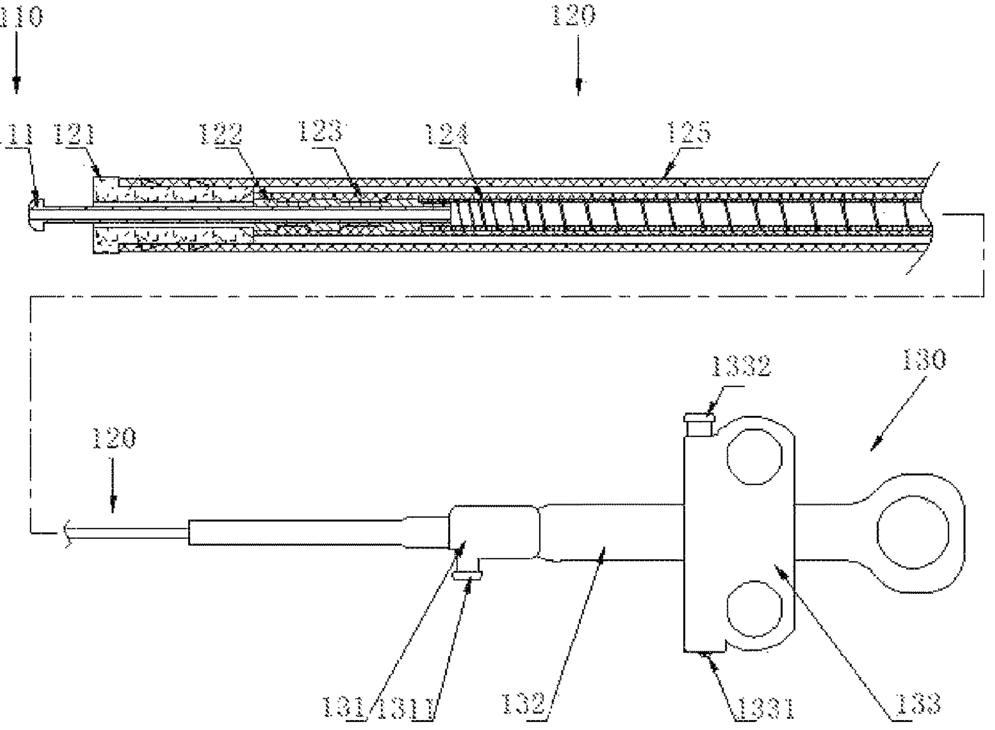
FIG. 2 is a schematic view of the device of the present disclosure when applied to a high frequency electric knife.

FIG. 2 is a schematic view of the device of the present disclosure when applied to a high frequency electric knife. The high frequency electric knife includes an electrode portion 110, a conveying portion 120, and an operating portion 130. An electrode 111 includes a hollow tubular part and a protrusion. The shape of the electrode is not limited to such a structure, and other structures with the hollow tubular part can be implemented. The hollow tubular part of the electrode can realize the functions of liquid passage, conveying powders, resection, and the like. A stopper 121 serves to insulate. The stopper 121 adopts a tubular structure, and is made of materials with heat resistance and insulating property such as zirconium oxide. The stopper 121 is fixedly connected with the distal end of an outer tube 125, and is used for limiting the extension and retraction of the distal end of the electrode 111, and the size of an inner aperture of the stopper 121 is larger than the outer diameter of the hollow tubular part of the electrode. The seal 122 is made of a conductive material, adopts a concave-convex structure that facilitates sealing, and is fixedly connected with the proximal end of the electrode 111. The seal 122 cooperates with the stopper 121 to limit an extension length of the electrode 111. The insulating layer 123 is made of an insulating material such as PTFE, covers on the surfaces of the seal 122 and the spiral tube 124, and has functions of sealing and insulating. The spiral tube 124 is made of a conductive material, and has a smaller resistance than a common wound spring tube, hence a larger current may be generated when a loop is formed, and the high frequency electric knife may achieve higher efficiency. The spiral tube 123 also provides a lumen. Given the same outer diameter, since the wall thickness is small, a larger lumen space can be provided for liquid injection or powder spraying. The outer tube 125 extends from the proximal end to the distal end and supports an internal connecting device, which facilitates pushing the electrode. The distal end of the outer tuber 125 is connected with the stopper 121, and the proximal end is fixedly connected with a positioning structure 131. The positioning structure 131 includes a Luer taper 1311 as an input port for a liquid or powder product. The reference numeral 132 denotes a core rod, and a slider 133 can slide back and forth along the core rod 132. The slider 133 is connected with the proximal end of the spiral tube 124, and the spiral tube 124 is controlled to extend or retract the active electrode 111. The slider 133 is further provided with a conductive connector 1331 and a Luer taper 1332. The conductive connector 1331 is connected with an external high-frequency generator, and the Luer taper 1332 is an input port for a liquid or powdery product. Herein, the spiral tube 124 adopts a structure combining the gradual-pitch and the equal-pitch configurations, and is designed to have a pitch that gradually decreases from the proximal end to the distal end. The pitch close to the distal electrode is smaller, which renders better flexibility and facilitates the high frequency electric knife passing through the curved channel of an endoscope. The pitch close to the proximal operating portion 130 is larger, providing better rigidity and support, hence a user is facilitated to insert the product into the endoscope lumen channel. A part of the non-spiral structural region is reserved close to the slider 133, which facilitates pushing to extend and retract the electrode 111. The spiral tube can also be provided with threads in an equal-pitch configuration, a gradual-pitch configuration, or a combination of various equal-pitch configurations according to requirements.

In use, the slider 133 is pulled to retract the electrode 111 to an end face of the stopper 121, and then the high frequency electric knife is inserted into the channel of an endoscope. The high frequency electric knife can smoothly pass through the distal bent structure of the endoscope because the pitch at the distal end of the spiral tube 124 is small. The proximal end of the spiral tube 124 has a larger pitch and is relatively rigid so that the user can push the high frequency electric knife towards the distal end of the endoscope. When the high frequency electric knife is brought into the field of view in the endoscope, the high-frequency electricity is conducted through the conductive connector. Since the seal 122 and the spiral tube 124 are conductive, the high-frequency electricity can be conducted to the electrode portion 110 for marking. After marking, the slider 133 is pushed to extend the electrode 111 for resection by virtue of the pushing effect of the non-spiral structural region at the proximal end of the spiral tube 124. In the resection, if liquid injection is necessary to elevate a mucosal tissue, a syringe can be externally connected at the Luer taper 1332 to inject liquid and elevate the tissue, whereby a liquid buffer layer, namely a "water cushion", is formed underneath the mucosal membrane. The "water cushion" effectively isolates the muscular layer and the lesion and effectively prevents heat conduction, clearing the surgical field of view and greatly reducing the risk of bleeding because blood vessels are squeezed and sealed by the water cushion. In case of tissue bleeding, the bleeding can be stopped and the bleeding site can be cleaned by means of liquid injection with an external syringe of the Luer taper 1332 or 1311 or spraying hemostasis powders, through the lumen channel of the hollow tubular part of the spiral tube 124 or a gap formed between the insulating layer 123 and the outer tube 125.

Embodiment 2

Figure 3:
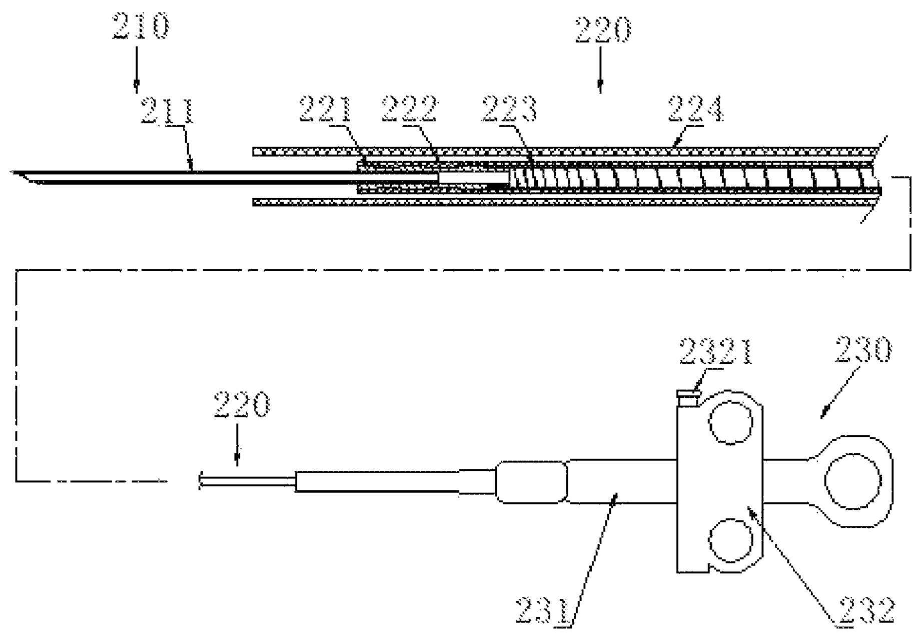
FIG. 3 is a schematic view of the device of the present disclosure when applied to an ultrasonic aspiration biopsy needle.

FIG. 3 is a schematic view of the device of the present disclosure when applied to an ultrasonic aspiration biopsy needle. The ultrasonic aspiration biopsy needle includes a puncturing portion 210, a conveying portion 220, and an operating portion 230. Herein, the reference numeral 211 denotes a puncturing needle, which adopts a hollow tubular structure, and includes a needle tip for puncturing to sample; the reference numeral 221 denotes a seal, which is of a non-planar structure favorable for sealing and is fixedly connected with the puncturing needle 211; an insulating layer 222 covers on the surfaces of the seal 221 and a spiral tube 223 and provides a sealing effect; an outer tube 224 extends from the proximal end to the distal end, supports an internal connecting device, and facilitates pushing the puncturing needle 211; a core rod 231 is connected with the proximal end of the outer tube 224, a slider 232 can slide along the core rod 231 and includes a Luer taper 2321. The spiral tube 223 adopts a structure combining the gradual-pitch and the equal-pitch configurations. The pitch close to the distal puncturing needle 211 is small, which renders proper flexibility and facilitates the whole biopsy needle passing through the curved channel of an endoscope. The pitch close to the proximal operating portion 230 of the spiral tube 223 is large and thus provides good support performance, and the user is facilitated to insert the ultrasonic aspiration biopsy needle into the endoscope lumen channel. A part of the non-spiral structural region is preserved at an end of the spiral tube close to the slider, which facilitates puncturing. The spiral tube can also be provided with threads in an equal-pitch configuration, a gradual-pitch configuration, or a combination of various equal-pitch configurations according to requirements.

In use, the biopsy needle is firstly inserted into the channel of the endoscope. The pitch of the spiral tube at the distal end of the ultrasonic aspiration biopsy needle is small, whereby the product is facilitated to pass through the curved structure at the distal end of the endoscope. The pitch of the spiral tube at the proximal end is large and relatively rigid, and the user is facilitated to push the product towards the distal end of the endoscope. When the ultrasonic aspiration biopsy needle enters the field of view in the endoscope, the length of the needle 211 extending out of the outer tube 224 can be controlled by adjusting the slider 232. Upon puncturing, a vacuum device is connected at the Luer taper through a channel of the spiral tube 223 to suck the tissue into the puncturing needle for sampling.

Embodiment 3

Figure 4:
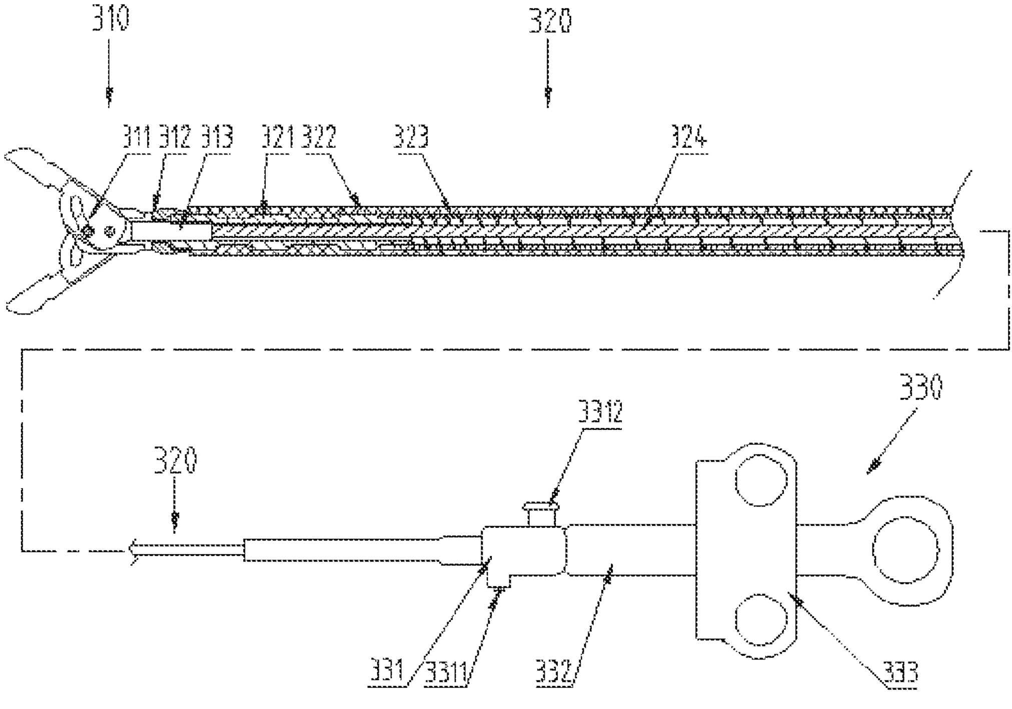
FIG. 4 is a schematic view of the device of the present disclosure when applied to a pair of hemostat forceps.

FIG. 4 is a schematic view of the device of the present disclosure when applied to a pair of hemostat forceps. The hemostat forceps include a clamping portion 310, a conveying portion 320, and an operating portion 330. Herein, the reference numeral 311 denotes a hemostat head, which is not limited to such a shape, but can be scissors-shaped and sawtooth-shaped. The hemostat head 311 is used for electrocoagulation hemostasis or resection, and is movably connected with a fixing seat 312. The fixing seat 312 is made of a conductive material, used for supporting the hemostat head 311 and facilitating the hemostat head 311 opening and closing smoothly, with its inner aperture being larger than the outer diameter of a pull rod 313. A seal 321 is made of a conductive material and is of a non-planar structure that is favorable for sealing, and the proximal end of the seal 321 is connected with the fixing seat 312. The reference numeral 322 denotes an insulating layer, which is made of PTFE and other insulating materials. The insulating layer 322 covers on the surfaces of the sealing part 321 and the spiral tube 323, and provides sealing and insulating effects. The spiral tube 323 is made of a conductive material, and has a smaller resistance than a common wound spring tube, hence a larger current may be generated when a current loop is formed, and higher efficiency may be achieved. The spiral tube has a smaller outer diameter than other similar products because it has a smaller wall thickness given the same inner diameter, so that the hemostat forceps can adapt to a smaller endoscope lumen channel. The reference numeral 324 denotes a pull cable, which is connected with the pull rod 313 at its distal end and can be a steel cable or a steel wire, used for driving to open or close the hemostat head 311. The reference numeral 331 denotes a positioning structure, connected with a conductive connector 3311 at its proximal end, used for connecting with a high-frequency power supply, conducting a high-frequency current to the hemostat head end through the spiral tube 323 to close the hemostat head 311 for electrocoagulation hemostasis. The reference numeral 332 denotes a core rod, a slider 333 can slide along the core rod 332, and the slider 333 can be pushed and pulled along the core rod to open and close the hemostat head 311. The spiral tube 323 adopts a structure combining the gradual-pitch and the equal-pitch configurations. The pitch close to the distal end is small, which renders proper flexibility and facilitates the whole hemostat forceps passing through the curved channel of an endoscope. The pitch close to the proximal end of the spiral tube 323 is large and thus provides good support performance, and the user is facilitated to insert the hemostat forceps into the endoscope lumen channel. A part of the non-spiral structural region is preserved at an end of the spiral tube close to the slider, which facilitates pushing. The spiral tube can also be provided with threads in an equal-pitch configuration, a gradual-pitch configuration, or a combination of various equal-pitch configurations according to requirements.

In use, the slider 333 is pulled to close the hemostat head 311, and then the distal end of the hemostat forceps is inserted into the channel of the endoscope. The pitch at the distal end of the hemostat forceps is small, which facilitates the product passing through the curved structure of the endoscope. The pitch at the proximal end of the spiral tube is large and is thus rigid, and the user is facilitated to push the hemostat forceps towards the distal end of the endoscope. When the hemostat forceps enter the field of view in the endoscope, high-frequency electricity can be conducted through a conductive connector 3311 to the hemostat head through the conductive function of the spiral tube 323. The slider 333 is pulled towards the proximal end to close the hemostat head 311 for electrocoagulation hemostasis. The external insulating layer 322 can provide insulating and protective effects. If a bleeding site seriously affects the surgical field of view, the bleeding site can be cleaned by means of liquid injection with an external syringe of a Luer taper 3312, through a gap formed between the hollow tubular part of the spiral tube 323 and the pull cable 324.

The foregoing is merely preferred embodiments of this application to enable those skilled in the art to understand or practice the disclosure of this application. Various modifications and combinations of these embodiments will be readily apparent to those skilled in the art, and the generic principles defined herein may be implemented in other embodiments without departing from the spirit or scope of the application. Therefore, this application is not intended to be limited to the embodiments shown herein but is to be accorded the widest scope consistent with the principles and novel features disclosed herein.

What is claimed is:

1. A medical connecting device having a proximal end and a distal end, comprising a continuous spiral tube and an insulating layer directly coated on an outer surface of the continuous spiral tube, the insulating layer forming an outermost layer of the device, wherein the continuous spiral tube integrates functions of electricity conducting and liquid passage, wherein the continuous spiral tube has a conductive hollow tubular structure made of a material with electrical conductivity, provides a channel to enable the function of liquid passage, and forms a current loop for conducting electricity to an instrument electric part connected at the distal end via the continuous spiral tube, wherein the continuous spiral tube consists of a middle spiral structural region, a distal non-spiral structural region extending distally from the middle spiral structural region, and a proximal non-spiral structural region extending proximally from the middle spiral structural region, with the distal non-spiral structural region, the proximal non-spiral structural region, and the middle spiral structural region all having hollow tubular structure made of a material with electrical conductivity, wherein the middle spiral structural region has a spiral structure with a pitch that gradually changes from a proximal end of the middle spiral structural region to a distal end of the middle spiral structural region, wherein the medical connecting device further comprises one or more seals provided at the distal non-spiral structural region or the proximal non-spiral structural region and connected with the distal non-spiral structural region or the proximal non-spiral structural region, wherein the insulating layer covers outer surfaces of the one or more seals, and wherein the one or more seals are of a non-planar structure of a concavo-convex type, a concave type, or a convex type.

2. The medical connecting device according to claim 1, wherein the pitch gradually decreases from the proximal end of the middle spiral structural region to the distal end of the middle spiral structural region, a smaller pitch at the distal end of the middle spiral structural region renders flexibility that facilitates passing through a curved channel of a medical apparatus, and a larger pitch at the proximal end of the middle spiral structural region provides support performance and facilitates pushing a medical instrument to the distal end of the middle spiral structural region.

3. The medical connecting device according to claim 1, wherein the pitch gradually decreases and then gradually increases from the proximal end of the middle spiral structural region to the distal end of the middle spiral structural region.

4. The medical connecting device according to claim 1, wherein the pitch gradually increases from the proximal end of the middle spiral structural region to the distal end of the middle spiral structural region.

5. The medical connecting device according to claim 1, wherein the convex portion of the non-planar structure may be a semicircle, a rectangle, a trapezoid, or a toothed shape.

6. The medical connecting device according to claim 1, wherein the insulating layer is made of a polymer material.

7. The medical connecting device according to claim 6, wherein the polymer material is polytetrafluoroethylene, fluoroethylene propylene copolymer, or polyethylene.

8. The medical connecting device according to claim 1, wherein the insulating layer is coated on the outer surface of the spiral tube through pyrocondensation, welding, or pasting.

9. A medical connecting device having a proximal end and a distal end, comprising a continuous spiral tube and an insulating layer coated directly on an outer surface of the continuous spiral tube, the insulating layer forming an outermost layer of the device, wherein the continuous spiral tube integrates functions of electricity conducting and liquid passage, wherein the continuous spiral tube has a conductive hollow tubular structure made of a material with electrical conductivity, provides a channel to enable the function of liquid passage, and forms a current loop for conducting electricity to an instrument electric part connected at the distal end via the continuous spiral tube, wherein the continuous spiral tube includes a middle spiral structural region, a distal non-spiral structural region extending distally from the middle spiral structural region, and a proximal non-spiral structural region extending proximally from the middle spiral structural region, with the distal non-spiral structural region, the proximal non-spiral structural region, and the middle spiral structural region all having hollow tubular structure made of a material with electrical conductivity, wherein the middle spiral structural region has a spiral structure with a pitch that gradually changes from a proximal end of the middle spiral structural region to a distal end of the middle spiral structural region, wherein the medical connecting device further comprises one or more seals provided at the distal non-spiral structural region or the proximal non-spiral structural region and connected with the distal non-spiral structural region or the proximal non-spiral structural region, wherein the insulating layer covers outer surfaces of the one or more seals, and wherein the one or more seals are of a non-planar structure of a concavo-convex type, a concave type, or a convex type.

10. The medical connecting device according to claim 9, wherein the insulating layer is coated directly on the outer surface of the spiral tube through pyrocondensation, welding, or pasting.

11. The medical connecting device according to claim 9, wherein the pitch gradually decreases and then gradually increases from the proximal end of the middle spiral structural region to the distal end of the middle spiral structural region.

12. The medical connecting device according to claim 9, wherein the convex portion of the non-planar structure may be a semicircle, a rectangle, a trapezoid, or a toothed shape.

13. The medical connecting device according to claim 9, wherein the insulating layer is made of a polymer material.

14. The medical connecting device according to claim 13, wherein the polymer material is polytetrafluoroethylene, fluoroethylene propylene copolymer, or polyethylene.

15. The medical connecting device according to claim 9, wherein the pitch gradually decreases from the proximal end of the middle spiral structural region to the distal end of the middle spiral structural region, a smaller pitch at the distal end of the middle spiral structural region renders flexibility that facilitates passing through a curved channel of a medical apparatus, and a larger pitch at the proximal end of the middle spiral structural region provides support performance and facilitates pushing a medical instrument to the distal end of the middle spiral structural region.

16. The medical connecting device according to claim 9, wherein the pitch gradually increases from the proximal end of the middle spiral structural region to the distal end of the middle spiral structural region.

* * * * *